(12) United States Patent
Kienzle, III (10) Patent No.: US 6,917,827 B2
(45) Date of Patent: Jul. 12, 2005

(54) ENHANCED GRAPHIC FEATURES FOR COMPUTER ASSISTED SURGERY SYSTEM

(75) Inventor: Thomas C. Kienzle, III, Lake Forest, IL (US)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 512 days.

(21) Appl. No.: 09/683,104

(22) Filed: Nov. 19, 2001

(65) Prior Publication Data

US 2002/0077540 A1 Jun. 20, 2002

Related U.S. Application Data

(60) Provisional application No. 60/249,695, filed on Nov. 17, 2000.

(51) Int. Cl.$^7$ .............................. A61B 6/00; A61B 17/56
(52) U.S. Cl. ............................ 600/427; 606/96; 606/97
(58) Field of Search .................. 378/20, 205; 600/427, 600/426; 606/130, 96, 97

(56) References Cited

U.S. PATENT DOCUMENTS

| | | |
|---|---|---|
| 4,305,394 A | 12/1981 | Bertuch, Jr. |
| 4,475,549 A | 10/1984 | Oh |
| 4,632,111 A | 12/1986 | Roche |
| 4,716,894 A | 1/1988 | Lazzeri et al. |
| 4,994,064 A | 2/1991 | Aboczky |
| 5,007,936 A | 4/1991 | Woolson |
| 5,251,127 A | 10/1993 | Raab |
| 5,562,448 A | 10/1996 | Mushabac |
| 5,638,819 A | 6/1997 | Manwaring |
| 5,682,886 A | 11/1997 | Delp |
| 5,748,767 A | 5/1998 | Raab |
| 5,880,976 A | 3/1999 | DiGioia |

(Continued)

OTHER PUBLICATIONS

C. Nikou, et al. "POP: Preoperative Planning and Simulation Software for Total Hip Replacement Surgery," published in the Proceedings of the Second International Conference on Medical Image Computing and Computer–Assisted Intervention, Cambridge, UK, 1999.

C. Nikou, et al. "Description of Anatomic Coordinate Systems and Rationale for Use in an Image–Guided Total Hip Replacement System," published in the Proceedings of the Third International Conference on Medical Image Computing and Computer–Assisted Intervention, Pittsburgh, 2000.

S. Nishihara, et al. "Measurement of Pelvic Tilting Angle during Total Hip Arthroplasty Using a Computer Navigation System," published in the Proceedings of the Third International Conference on Medical Image Computing and Computer–Assisted Intervention, Pittsburgh, 2000.

*Primary Examiner*—Shawna J. Shaw
(74) *Attorney, Agent, or Firm*—McAndrews, Held & Malloy, Ltd.; Peter J. Vogel; Michael A. Dellapenna (57) ABSTRACT

A computer assisted surgery system with is enhanced graphics features is described for assisting a surgeon in orthopaedic procedures. A system is described for use in inserting multiple guide pins in hip fracture surgery using a single bore drill guide that has a graphical representation comprising its real trajectory and one or more virtual trajectories, the virtual trajectories representing potential positions of other guide pins to be placed during the procedure. Additionally, representations of inserted guide pins and virtual trajectories may be retained on the display at their inserted positions for use in aligning subsequent guide pins. A system is also described for orientation of an acetabular cup in a total hip replacement surgery. During cup insertion, the surgeon is provided with information regarding the orientation of the cup with respect to a pelvic reference frame that is based on accepted pelvic landmarks. The positions of each landmark is calculated by the system when a probe with a virtual tip, separate from its physical tip, is overlaid on the landmark in roughly orthogonal images of the pelvis.

6 Claims, 12 Drawing Sheets

U.S. PATENT DOCUMENTS

| | | |
|---|---|---|
| 6,006,126 A | 12/1999 | Cosman |
| 6,063,124 A | 5/2000 | Amstutz |
| 6,064,904 A | 5/2000 | Yanof |
| 6,069,932 A | 5/2000 | Peshkin |
| 6,214,014 B1 | 4/2001 | McGann |
| 6,285,902 B1 * | 9/2001 | Kienzle et al. ............. 600/427 |
| 6,302,890 B1 | 10/2001 | Leone, Jr. |
| 6,477,400 B1 * | 11/2002 | Barrick ....................... 600/426 |
| 6,671,538 B1 * | 12/2003 | Ehnholm et al. ........... 600/425 |
| 2001/0034530 A1 * | 10/2001 | Malackowski et al. ..... 606/130 |
| 2002/0095083 A1 * | 7/2002 | Cinquin et al. ............. 600/407 |

\* cited by examiner

ENHANCED GRAPHIC FEATURES FOR COMPUTER ASSISTED SURGERY SYSTEM

BACKGROUND OF INVENTION

This invention relates to a computer assisted surgery system with enhanced graphics capabilities for use in inserting multiple screws into a hip fracture and orienting a total hip acetabular component.

Fractures of the femoral neck, one kind of hip fracture, are a common injury of the elderly with over 150,000 such fractures occurring annually. The currently accepted treatment for mildly displaced femoral neck fractures is surgical fixation. In the procedure, three cannulated screws are inserted in the hip, from the lateral aspect of the femur, across the fracture site and into the femoral head. The initial step is the placement of three guide pins, over which the screws are inserted, in a characteristic triangular pattern. This is typically performed under fluoroscopic guidance, usually with the aid of a drill guide. Some surgeons prefer to use a drill guide with a single bore, but doing so may make it difficult to achieve the desired triangular spacing and optimum placement of the guide pins in the femoral neck. Other surgeons prefer a drill guide with multiple bores that are fixed in the proper triangular spacing, but this requires a larger incision and doesn't permit the surgeon much flexibility to modify the preset pattern. With either drill guide, it can be difficult to accurately predict the final guide pin placement. Further, the surgery requires a significant number of fluoroscopic images and x-ray exposure for the surgeon, patient and operating room staff.

Fluoroscopic based image guided surgery systems can be of benefit in predicting the paths of the guide pins and in significantly reducing the amount of radiation exposure. Image guided systems such as those taught in U.S. Pat. Nos. 5,772,594 and 6,285,902, incorporated herein by reference, employ a computer and a localizing device to track a drill or drill guide and superimpose a trajectory line on fluoroscopic images. U.S. Pat. No. 6,285,902 describes a system in which, preferably, orthopaedic surgical tools outfitted with infrared LEDs are tracked by an optical localizing device. The poses of these tools are determined and graphic representations of the tools are superimposed on standard intra-operative x-ray images. This allows the surgeon to view, in real time, the position of the tool or tools with respect to an imaged body part or another tool or tools. In the preferred embodiment, a drill guide outfitted with infrared LEDs is tracked and the trajectory of its bore is displayed on the x-ray image of the involved bone. This allows a surgeon to accurately predict the trajectory of a guide pin that passes through the bore of the drill guide. The surgeon can see the path each guide pin will take and can improve the accuracy and speed of insertion of the guide pin with only a minimum number of x-ray images. These systems, however, do not provide help in selecting paths that will lead to the desired triangular pattern with proper spacing between screws. On the other hand, a tracked drill guide with multiple bores may be used, but this requires a large incision and does not leave the surgeon with flexibility in the spacing or orientation (e.g., parallel vs. diverging) of the screws.

Another surgery that is very common in the elderly is total hip replacement. Over 200,000 total hip surgeries are performed each year. This procedure replaces the natural ball and socket joint of the hip, with a metal ball attached to the femur and a plastic lined cup in the socket (acetabulum) of the pelvis. A crucial step in the procedure is the proper alignment of the acetabular cup relative to the pelvic anatomy. Cups that are not properly oriented can lead to dislocation of the new hip and may require reoperation to reorient the cup. However, it can be quite difficult to orient the acetabular cup correctly. Even though the acetabulum is typically fully exposed, and the surgeon has the freedom to place the cup in any orientation, the pelvic landmarks that would give the surgeon the proper frame of reference are not exposed. One such set of landmarks in common usage for defining a pelvic reference frame (albeit for evaluation purposes in post-operative x-rays) are the left and right anterior superior iliac spines (ASIS) and the anterior portion of the pubic bone. During surgery, however, these are not exposed and are thus hidden under sterile draping material and the patient's soft tissue. This problem is even worse with obese patients. Further, the pelvis may be tilted relative to the operating table, making it difficult to use the table or any vertical or horizontal plane as a reliable reference. This leaves the surgeon to orient the acetabular component based on very limited information: the pelvic anatomy exposed in the immediate vicinity of acetabulum, the general body orientation, any visual or palpable evidence of the orientation of the pelvis, and any other clues the surgeon can extract based on experience.

Numerous surgical instruments have been introduced with features designed to assist the surgeon in orienting the acetabular component. U.S. Pat. No. 4,475,549 describes one such instrument, in which handles are oriented such that the cup is properly oriented when the handles are aligned with the patient axis. Again, however, this requires that the surgeon correctly identify the alignment of the patient (i.e., of the patient's pelvis) under the drape and soft tissue.

Image guided techniques have also been applied to the problem of acetabular cup orientation. U.S. Pat. No. 6,002, 859 teaches a system for orienting the acetabular cup that is based on a CT scan to preoperatively construct a 3-D model of the pelvis and plan the placement of the acetabular component. During surgery, a registration step is required to correlate the position of the patient's pelvis with the 3-D model. This currently requires the sampling of several points on the patient with a probe and their correlation to the 3-D model. While this system can improve the accuracy, and even the surgical outcome of the total hip procedure, it requires a CT scan which is not currently required, and a potentially time consuming intraoperative registration step.

SUMMARY OF INVENTION

Accordingly, one objective of the present invention is to provide a computer assisted surgery system with enhanced graphic features for assisting a surgeon in positioning multiple guide pins in a bone as part of a hip fracture fixation surgery and in orienting an acetabular cup during a total hip replacement surgery.

Another objective of the invention is to provide a technique and apparatus for displaying a graphic representation of a drill guide that includes a real trajectory corresponding to the bore of the drill guide and one or more virtual trajectories relative to the actual trajectory that indicate possible other drill guide trajectories.

Another objective of the invention is to provide a technique and apparatus for displaying graphic representations of implants or instruments in positions retained from previous steps of the procedure.

Still another objective of the invention is a method and apparatus for accurately orienting an acetabular component relative to the pelvis in a total hip replacement surgery.

Still another objective of the invention is a method and apparatus for noninvasively determining the location of bony landmarks inside a patient's body.

These and other objects of the present invention are achieved by the use of a computer assisted surgery system, including a computer, a localizing device and a display monitor. The system also includes a drill guide for use in placing multiple guide pins for hip fracture surgery and a probe and positioning instrument for use in orienting an acetabular cup. The poses of all three instruments are measurable by a localizing device. The system is improved for use in the femoral neck fracture surgery and acetabular cup orientation procedure by two enhancements to the graphic capabilities of the original computer assisted surgery system.

The first enhancement is inclusion in the instrument representation of features that are not physically present on the instrument, but that provide additional information and functionality to the surgeon. While these virtual features are visible only in the graphic representation, their poses are related to the poses of real features of the instrument and their poses in space can be calculated. A virtual feature may represent a physical feature that is typically present on a conventional instrument but removed in the instrument under consideration. A virtual feature may also represent a physical feature that would improve the function of an instrument but cannot be added, or are not desirable to add, because of physical constraints, instrument simplicity, or other reasons (e.g., a long probe tip for indicating points inside of tissues) but whose function instead can be sufficiently simulated with appropriate modeling in the instrument's graphic representation. Further, virtual features may include modeling of physical features that are present on physical instruments at other times during the surgery or modeling of physical features that are located at other poses during other steps of the surgery and are related in position to the instrument being used in the current step (e.g., guide pin trajectories of past or future steps of the procedure). The representation of features virtually instead of physically allows the surgeon to benefit from the additional positioning information while still promoting simpler instruments and less invasive surgical technique.

The second enhancement to the graphics features is the ability to retain a version of the instrument representation on the display in the position that it occupied at a given point in time. This allows the surgeon to view representations of previously placed hardware (e.g., guide pins) without requiring the acquisition of new x-ray images. Further, virtual features may also be retained in order to carry over information from one step of the procedure to another (e.g., template information or planning markings) or to indicate the location of previously identified positions (e.g., selected landmarks or fiducials).

During the placement of guide pins in the hip fracture surgery, a drill guide is used with a graphic representation that comprises a real trajectory that corresponds to the bore of the drill guide and that shows the path a guide pin will take when inserted with the drill guide at its present position. The graphic representation further comprises one or more virtual trajectories that are defined relative to the real trajectory and represents other possible positions for guide pins. Preferably, the virtual trajectories are the other two positions of the desired triangular pattern of parallel guide pins typically used in femoral neck fracture fixation. The virtual trajectories can be redefined by the surgeon to achieve any desired pattern and spacing of the guide pins. During surgery, the surgeon uses the computer assisted surgery system to insert the first guide pin by aligning the pattern of real and virtual trajectories in an appropriate position over the x-ray images of the femoral head and neck. Subsequent guide pins are inserted by aligning the virtual trajectories with x-ray images of the femur and previously placed guide pins. Alternatively, representations of previously placed guide pins and virtual trajectories are retained and the subsequent guide pin placements are made by aligning the actual trajectory of the drill guide with the retained virtual trajectories. This invention has the advantages of assisting the surgeon in achieving a desired screw pattern, permitting a small incision with a single bore drill guide, and allowing the surgeon flexibility in placing the guide pins.

During the procedure to orient the acetabular cup, a probe is used to identify the location of three landmarks on the pelvis. The graphic representation of the probe includes a virtual tip, at a fixed and known distance from the real tip of the probe. Two roughly orthogonal x-ray views of the pelvis are obtained and the probe is moved, always above the skin, in the vicinity of the bony landmark, until a graphic representation of the virtual probe tip overlays the image of the landmark in both x-rays, and the 3-D position of the landmark is calculated. This process is preferably performed for both anterior superior iliac spines and the anterior pubis and a pelvic coordinate frame is established. A positioning instrument with attached acetabular cup is tracked by the localizer and the system provides both a graphic representation of the orientation of the acetabular cup over the x-ray images and an alphanumeric readout of two calculated angular orientation values familiar to the surgeon. This invention has the advantages of non-invasively identifying accepted landmarks for establishing a pelvic reference frame, of automatically registering the images, and of not requiring a CT scan prior to surgery.

DETAILED DESCRIPTION

Figure 1A:
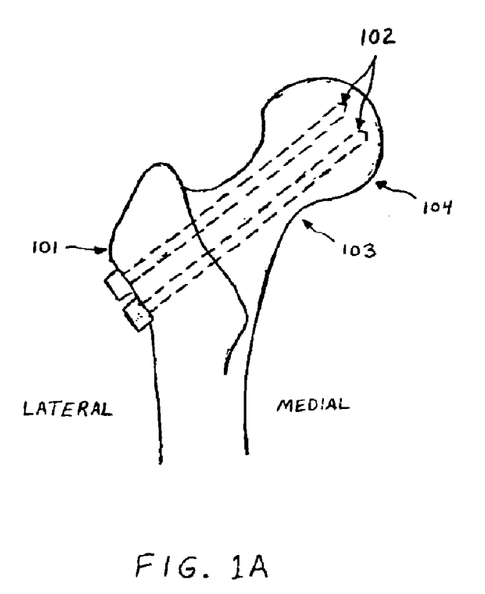
FIG. 1 illustrates the femur with inserted cannulated screws as an example of prior art.
Figure 1B:
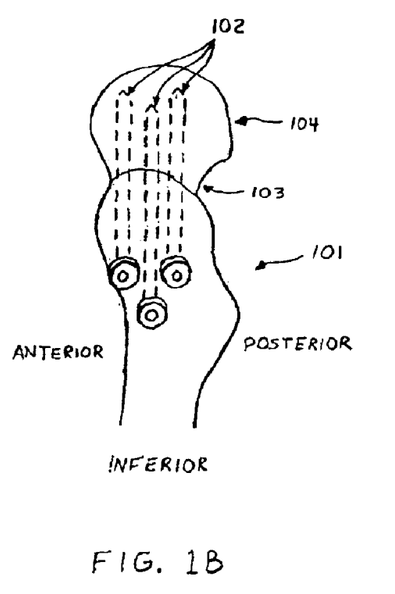

Current surgical practice for the treatment of a femoral neck fracture is the insertion of three cannulated screws through a small incision on the lateral (side) aspect of the hip. As shown in FIG. 1A, the screws (102) are inserted from the lateral aspect of the trochanteric area of the femur (101) through the femoral neck (103) and into the femoral head (104) in a roughly parallel manner. When observed from a lateral view, FIG. 1B, the screws describe the vertices of a triangle with one screw placed inferiorly (toward the knee), one placed anteriorly (toward the front) and one placed posteriorly (toward the back).

Figure 2:
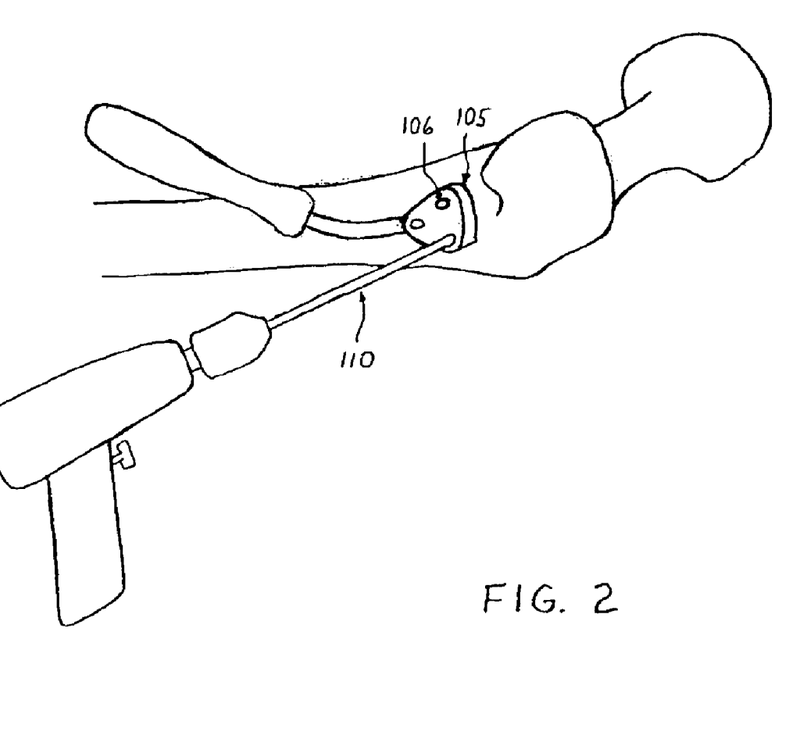
FIG. 2 illustrates the femur, drill and drill guide as an example of prior art.

The first step of the procedure, shown in FIG. 2, is the insertion of three guide pins (110) under fluoroscopic guidance. Numerous x-ray images involving frequent reorientation of the fluoroscope are required to monitor the progress of the guide pin insertion in both AP (front-to-back) and lateral (side) views. A drill guide (105) with three or more holes (106) is typically used to assist in keeping the guide pins (110) roughly parallel during the insertion.

Figure 3:
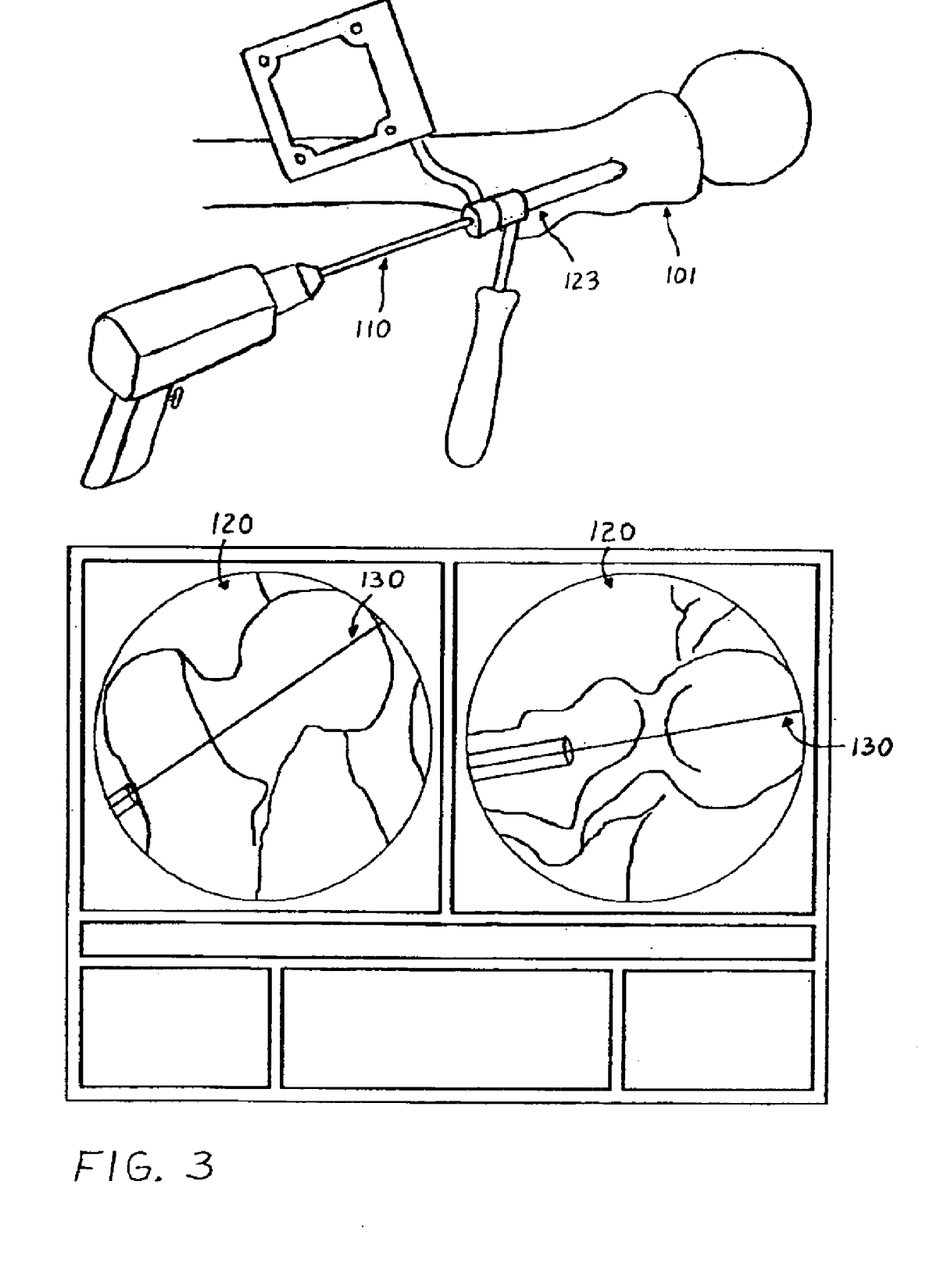
FIG. 3 illustrates the femur, drill and drill guide and an example of a screen display of two images and superimposed instrument representation.

As shown in FIG. 3, the computer assisted surgical system described in the previous application can assist the surgeon in this procedure by superimposing a graphic representation (130) of the drill guide (123) on the images (120) of the femur (101). The surgeon aligns the drill guide representation (130) such that the guide pin (110) will be inserted in a position that accommodates the remaining two guide pins in the desired triangular pattern. Once the drill guide (123) is properly aligned, the surgeon inserts the first guide pin (110) and obtains new AP and lateral x-rays (120) to show the final position of the guide pin (110) relative to the bone (101). The remaining two pins are inserted in a similar fashion with the surgeon using the drill guide representation (130) to align the drill guide (123).

Figure 4:
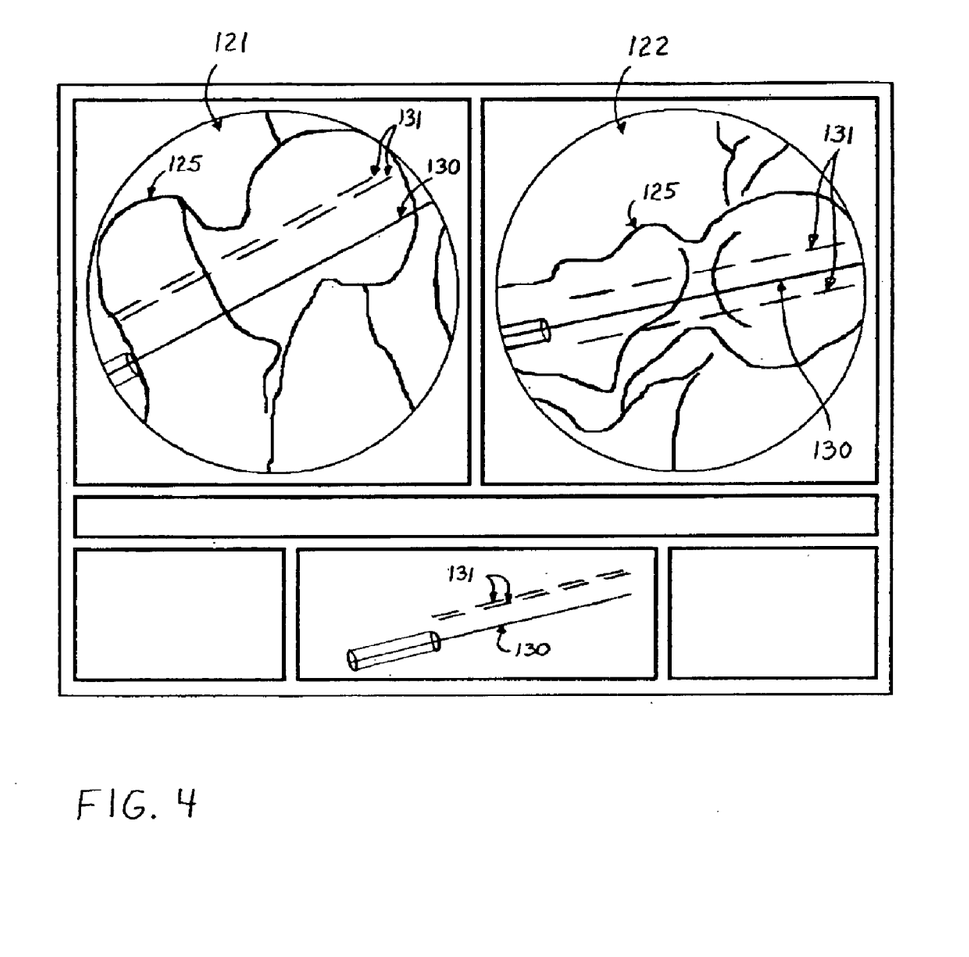
FIG. 4 is an example of a screen display of two images and superimposed actual and virtual trajectories.

The current invention augments the capability of the computer assisted surgery system by providing additional information to the surgeon in a novel manner. Whereas prior art systems display information directly related to physical features of the drill guide, the preferred embodiment of the current invention includes information that is not directly derived from a physical feature of the instrument. FIG. 4 shows the improved graphic representation (130, 131) of the same drill guide (123) which, in addition to a real trajectory (130) corresponding to the sleeve of the physical drill guide, also includes virtual trajectories (131) representing possible positions for the other two guide pins required in the surgery. Preferably, these virtual trajectories (131) take the form of dashed lines, but may be displayed in any manner that allows for their differentiation from the real trajectory (130) without departing from the instant invention. Preferably, three different representations are available for use in placement of the pin in the inferior, anterior, or posterior positions. The representation of the drill guide for placement of the inferior guide pin contains two virtual trajectories (131) located superior to the real drill guide trajectory (130). For placement of the anterior guide pin, the virtual trajectories (131) are located posterior to the real trajectory (130) while for posterior guide pin placement the virtual trajectories (131) are located anterior to the real trajectory (130). Alternatively, if the pin pattern is symmetric and the drill guide is sufficiently able to rotate, a single representation may be used by physically rotating the drill guide about its trajectory axis. Other representations, with alternative spacing and orientation of the virtual trajectories (131) relative to the real drill guide trajectory (130), may be made available to the surgeon to accommodate a range of bone sizes, fracture patterns, or surgeon preferences.

As the surgeon positions the drill guide against the femur, the guide's real trajectory (130) and the two virtual trajectories (131) are superimposed on the images (121 and 122) of the femur. With the virtual trajectories (131) included in the instrument representation, the surgeon is able to see relative to the femur image (125) how the positioning of the first pin will affect the positioning of the final three-pin pattern. In the preferred embodiment, the first guide pin placed is the inferior one. Alternatively, any pin placement order with corresponding drill guide representations may be used. With the guide's real trajectory (130) shown on the display in its proper position relative to the femur image (125), the surgeon then inserts the guide pin (110) through the drill guide (123), and advances it into the bone (101).

Figure 5:
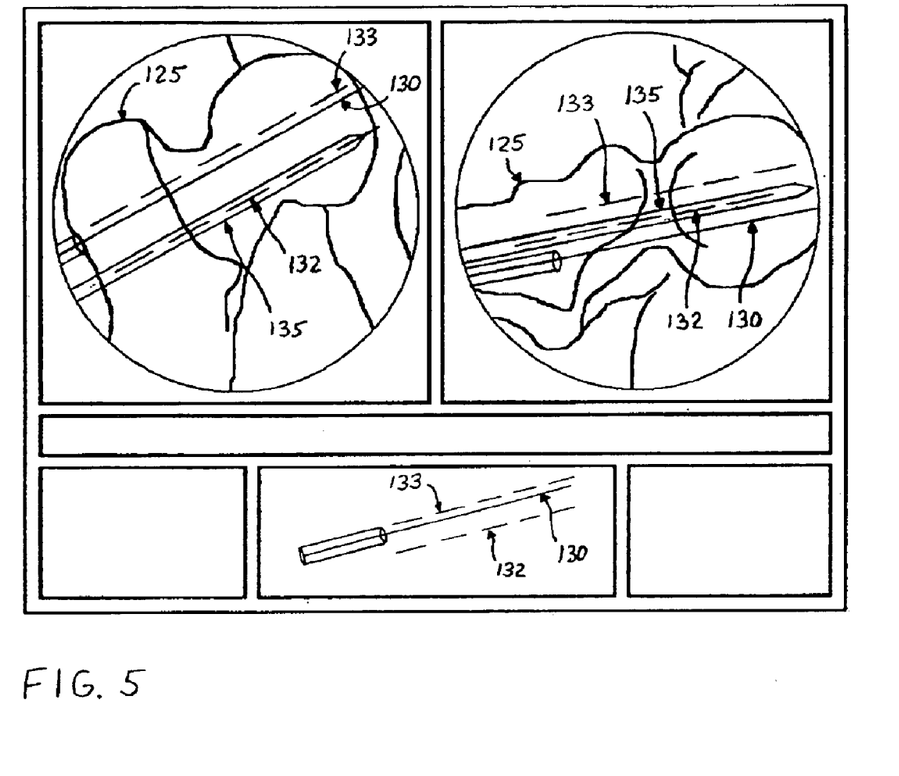
FIG. 5 is an example of a screen display of two images, superimposed actual and virtual trajectories and inserted guide pin.

Once the first guide pin is inserted, new x-ray images are obtained. As shown in FIG. 5 these images show the actual position of the first guide pin (135). In preparation for the placement of the second guide pin, the representation (130, 132 and 133) of the drill guide is changed to one for posterior pin placement. In the preferred embodiment, the drill guide's real trajectory (130) represents that of the posterior guide pin, while one virtual trajectory (132) represents the position of the previously placed inferior guide pin (135) and the other virtual trajectory (133) represents the proposed trajectory of the future anterior pin. Preferably, the surgeon aligns the drill guide (110) with the femur (101) such that the inferior virtual trajectory (132) overlays the image of the previously placed guide pin (135), while the other virtual trajectory (133) and the real trajectory (130) are aligned into their proper positions relative to the femur image (125). Then, the surgeon again advances the guide pin (110) through the drill guide (123) and into the bone (101).

Figure 6:
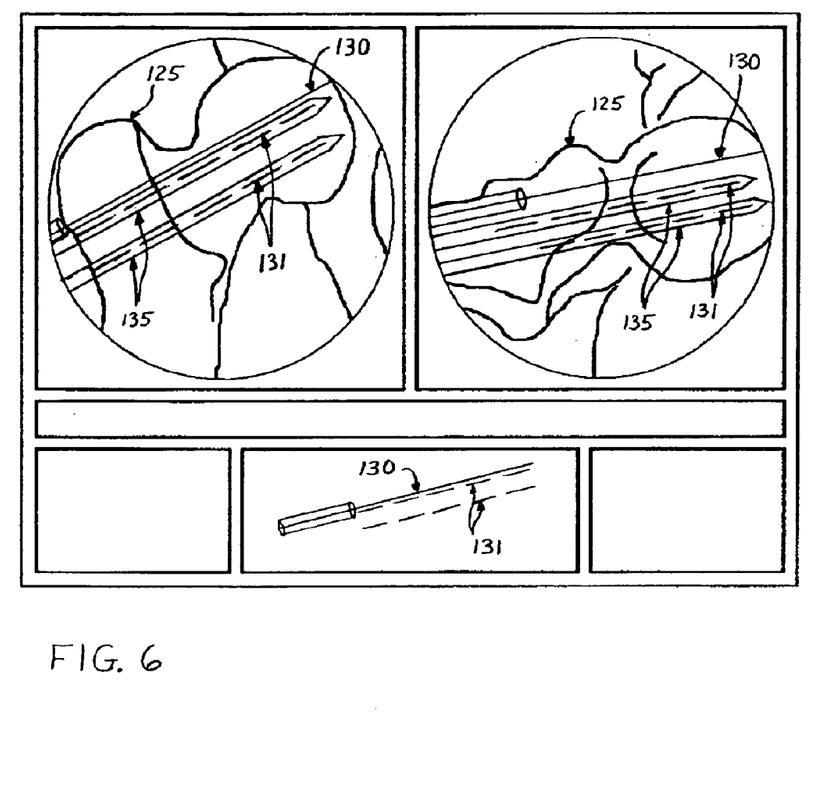
FIG. 6 is an example of a screen display of two images, superimposed actual and virtual trajectories and inserted guide pins.

Once the first two guide pins have been placed, new x-ray images are acquired as shown in FIG. 6. In the preferred embodiment, the representation of the drill guide is changed to show the virtual trajectories (131) inferiorly and posteriorly while the drill guide's real trajectory (130) is displayed anteriorly. Preferably, the surgeon aligns the virtual trajectories (131) to overlay the images of the previously placed pins (135) and advances the guide pin (110) through the drill guide (123) and into the bone (101). The remainder of the procedure, including the placement of the cannulated screws over the guide pins (110), is performed in the usual manner.

In any of the guide pin placement steps described, the surgeon should use good clinical judgment as to whether to follow the virtual trajectories exactly, to use them merely as reference marks, or to simply ignore them.

The major advantage of this invention is its ability to assist the surgeon in positioning multiple guide pins relative to one another without the necessity of a multi-bore mechanical jig. By using a single-bore drill guide to accurately place these pins, a smaller skin incision may be used, resulting in less trauma to the patient, faster healing, less risk of infection, and other advantages of minimally invasive surgery.

In the foregoing description, the assumption is made that the body part is held immobile throughout the procedure. Alternatively, a tracking device may be rigidly affixed to the bone and any changes in the pose of the bone during the procedure may be recorded and compensated for. This device may be comprised of three LEDs affixed to an assembly that is attached to the pelvis with one or more screws. However, any device that attaches rigidly to the femur and tracks its changes in pose may be used. As the tracking device changes pose, indicating a change in pose of the femur, the software adjusts the pose of the instrument representation being overlaid on the x-ray images in order to maintain accurate relative superpositioning.

While the above description of the invention relates to insertion of cannulated screws in the fixation of a femoral neck fracture, those skilled in the art will recognize its applicability to numerous other surgical procedures. In alternative embodiments, the drill guide may be replaced by a probe, a drill, a bone saw, an implant positioner, or any other surgical instrument. The drill guide trajectory may be replaced by a representation of a probe tip, a drill bit, a saw blade, an implant, or any other physical feature of a surgical instrument or implant attached to a surgical instrument. The virtual guide pin trajectories may be replaced by graphics that represent measurements, markings, or modeling of surgical instrument features not necessarily present on the instrument being used nor related to an existing physical feature of the instrument.

The virtual features may include graphics relating to another implant or instrument not currently affixed to the first implant or instrument, but whose position is ultimately related to it. The other implant or instrument may be used simultaneously with the first implant or instrument or may be involved with another step in the procedure, either before or after the current step. Additionally, the virtual feature may be derived from a physical feature that has been removed from an instrument or implant or it may represent an alternative configuration or state of the current instrument or implant. The virtual feature may comprise any representation that is not directly derived from the current physical properties of the instrument or implant that it represents without departing from the instant invention.

In the preferred embodiment, the graphic representations are displayed overlaid on x-ray images. Alternatively, the representations can be displayed overlaid on other medical imaging data (CT, MRI, etc.) or relative to other instruments or implants in a graphic picture not requiring imaging data.

Figure 7:
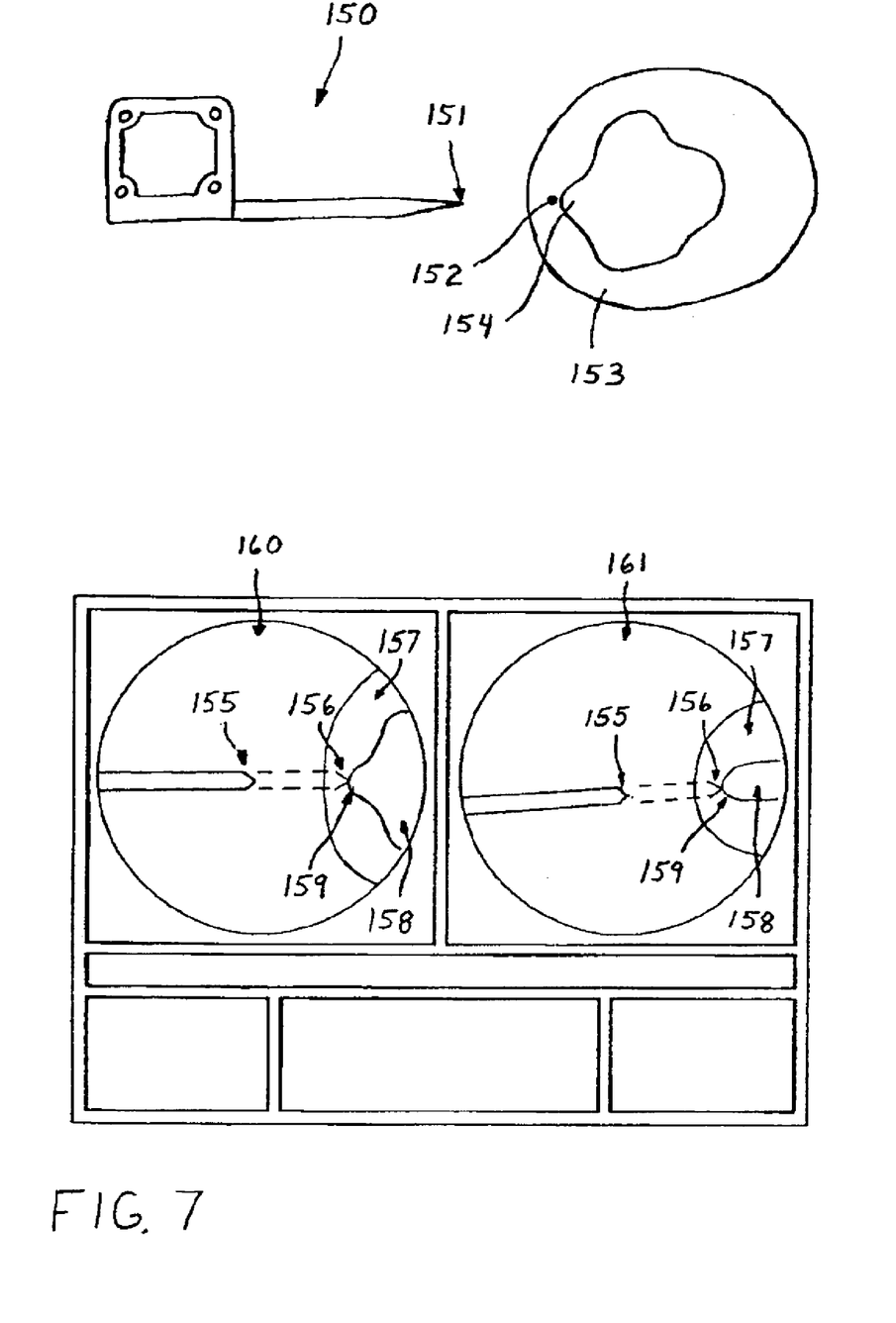
FIG. 7 illustrates a probe and body landmark with surrounding soft tissue and an example of a screen display of two images with a superimposed representation of the probe.

In another example, an instrument with a virtual feature is used to noninvasively determine the locations of specific points, structures, or landmarks within the body. Often in orthopaedic procedures it is desirable to identify the position of bony landmarks that are hidden by soft tissue, in order to establish a body reference frame. Current art, which includes directly touching landmarks by a probe, is not applicable in this case because the landmarks are covered by soft or bony tissue and therefore inaccessible to the tip of a probe. Therefore, the current invention, as shown in FIG. 7, includes a probe (150) which has a graphic representation that includes a real probe tip portion (155) and a virtual probe tip portion (156). The real probe tip portion of the representation (155) correlates directly with the position of the real probe tip (151). The virtual probe tip portion of the representation (156) correlates with a point in space (152) that is located in a fixed and known relationship to the physical probe tip (151).

In order to identify the location of a bony landmark (154) surrounded by soft tissue (153) two x-ray images (160 and 161) are obtained. Preferably the two images (160 and 161) are 90 degrees apart from one another, but may be any suitable angle apart without departing from the instant invention. The surgeon then positions the probe (150) in space, relative to the bony landmark (154) such that the tip of the virtual cursor (156) is coincident with the bony landmark's image (159) in both views (160 and 161) simultaneously. The surgeon then presses a footswitch, or activates some other signaling device, and the 3-D position of the point in space (152) corresponding to the virtual probe tip (152), and therefore the 3-D position of the bony landmark (154), is calculated and recorded in the computer's memory.

Alternatively, the virtual probe representation can be replaced with a straight line, a curved line, a plane, a curved surface, or some other graphic that allows for the alignment of the virtual probe with one or more landmarks or points. Further, those skilled in the art will recognize that the identification of landmarks or points with the virtual probe is applicable to other surgeries and other imaging modalities.

Figure 8:
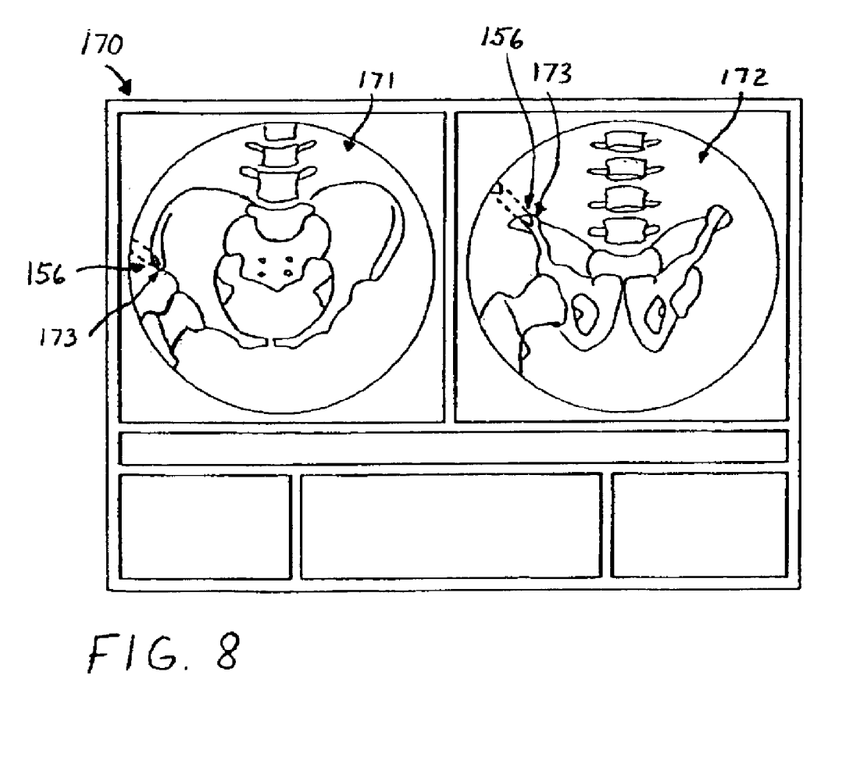
FIG. 8 illustrates a pelvis and probe and an example of a screen display with two images of the pelvis with a superimposed representation of the probe.

In a preferred embodiment, the purpose of identifying landmarks with the virtual probe is to establish a coordinate frame on a patient's pelvis relative to which is oriented the acetabular component in total hip replacement surgery. The patient is placed on his or her side on the operating room table and draped in the usual fashion. The surgeon then makes the usual incision and prepares the femur and pelvic acetabulum in the standard fashion. In the preferred embodiment, shown in FIG. 8, two modified AP x-ray images (171 and 172) of the patient's pelvis (181) are acquired by the C-arm fluoroscope and shown on the display (170). The first image (171) is an "inlet view" of the pelvis (181) taken with the C-arm aimed obliquely, approximately 40 degrees, from cephalad and anterior to caudal and posterior. The second image (172) is an "outlet view" of the pelvis (181) taken with the C-arm aimed from caudal and anterior to cephalad and posterior. The surgeon then uses a probe (150) outfitted with localizing emitters (177) to identify three landmarks (182, 183 and 184) by positioning the probe (150) in such a manner that the virtual probe tip (156) overlays the image (173) of the first bony landmark (183) in both views (171, 172). By pressing the footswitch, the system reads the pose of the probe (150) and calculates and records the three-dimensional location of the landmark (183). In this manner, the surgeon records the positions of the left anterior superior iliac spine (ASIS) (182), the right ASIS (183) and the top of the pubic symphysis (184). Alternatively, other bony landmarks may be selected without departing from the instant invention.

Figure 9:
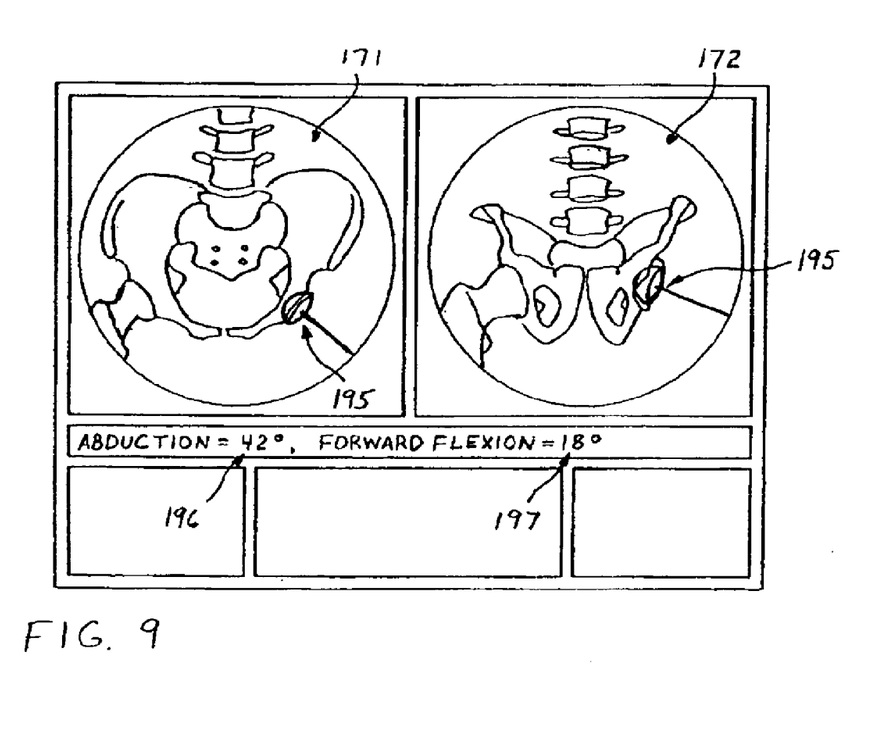
FIG. 9 illustrates a pelvis with reference planes and a positioning instrument and an example of a screen display of two images of the pelvis superimposed with a representation of the positioning instrument and text messages.

As shown in FIG. 9, the three landmarks (182, 183 and 184) are used to define a pelvic coordinate system. The first axis (185) of the pelvic coordinate system is contained in a line between the left ASIS (182) and right ASIS (183), a second axis (186) is perpendicular to the first axis and extends through the top of the pubic symphysis (184), and the third axis (187) is orthogonal to the first two axes (185 and 186). The "frontal" plane (188) is defined by the first two axes (185 and 186) and is considered by many orthopaedic surgeons to represent the standard vertical plane of the pelvis (181) during ambulation. Likewise, the axial plane (189) is defined by the first and last axes (185 and 187); and a third plane, the sagittal plane (not shown), is defined by the last two axes (186 and 187). Alternatively, other axes and planes may be defined without departing from the instant invention.

The surgeon then attaches an acetabular component (190) to a positioning instrument (191) outfitted with localizing emitters (192) and then places the component (190) into the patient's prepared acetabulum (179). The system displays a representation (195) of the positioning instrument (191) with the attached acetabular component (190) superimposed on the two images (171 and 172) by using the stored conic projection model of the C-arm. As the surgeon moves the positioning instrument (191), the display is updated in real time to show, graphically, the pose of instrument and implant representation (195) relative to the images of the pelvis.

At the same time, preferably, angular values (196 and 197) are calculated and displayed to quantify for the surgeon the orientation of the implant (190) relative to the pelvic landmarks (182, 183 and 184). The implant axis (193) is defined as the axis normal to the plane of the rim of the acetabular implant (190). Preferably this axis (193) is coincident with the long axis of the positioning instrument (191). The first value (196), the "abduction angle" is the angle between the implant axis (193) and the second axis (186) when both axes (193 and 186) are projected on the frontal plane (188). A second value (197), the "forward flexion angle" is the angle between the implant axis (193) and the inter-ASIS axis (185) when both axes are projected on the axial plane (189). Preferably, these values (196 and 197) are calculated continuously and displayed in numerical form in real time. Alternatively, other angles or values of interest to the surgeon may be calculated. These values may be displayed in numerous ways including numeric messages or graphic representations of angles or distances.

Optionally, views of the pelvis from points of view other than those available from the C-arm fluoroscope may be simulated and the orientation of the implant positioning instrument displayed relative to this simulated image. These simulated images may include lateral or axial views of the pelvis and may include any of a number of forms including bitmap pictures, previously obtained x-rays, or projections of CT data. A graphic representation of the implant positioning instrument is appropriately scaled and projected onto a plane that corresponds to that of the image. The representation is centered on the acetabulum and as the orientation of the implant positioning instrument is changed, its representation is reoriented in real time relative to the simulated image.

Once the surgeon has placed the acetabular component (190) into the proper orientation, an impacting device is used to press-fit the implant (190) into the acetabulum (179). The rest of the procedure, including final sizing of the components and closure of the incision is performed in the usual fashion.

In the foregoing description, the assumption is made that the body part is held immobile throughout the procedure. Alternatively, a tracking device may be rigidly affixed to the bone that records any changes in pose of the bone during the procedure. This device may be comprised of three LEDs affixed to an assembly that is attached to the pelvis with one or more screws. However, any device that attaches rigidly to the pelvis and tracks its changes in pose may be used. As the tracking device changes pose, indicating a change in pose of the pelvis, the software adjusts the pose of the instrument being overlaid on the x-ray images in order to maintain accurate relative superpositiong.

In alternative embodiments, other information regarding the fit and sizing of the implant is developed. In one alternative embodiment, the surgeon attaches an array of tracking emitters to the shaft of the femur prior to dislocating the hip and removing the femoral head. The surgeon presses the footswitch while rotating the femur around the femoral head, causing poses of the tracking array to be recorded. The location of the center of the femoral head relative to the tracking array is calculated by methods known in the art. Once the femoral and acetabular components have been placed, the sampling process and calculations are repeated. The software then compares the data recorded before and after the placement of the prosthetic components to provide information to the surgeon regarding the preservation of leg length, femoral offset, or other geometries of the replaced hip. Stored models of the implants used may be incorporated into these calculations to improve the accuracy and usefulness of this information.

Numerous other image-guided surgical procedures can make use of the virtual probe as a means of identifying the locations of internal landmarks. This invention has utility in any case where the location of a point is to be determined, but it is impossible or undesirable to touch the point directly with a probe tip. Those skilled in the art will recognize the applicability of this invention to other procedures.

Figure 10:
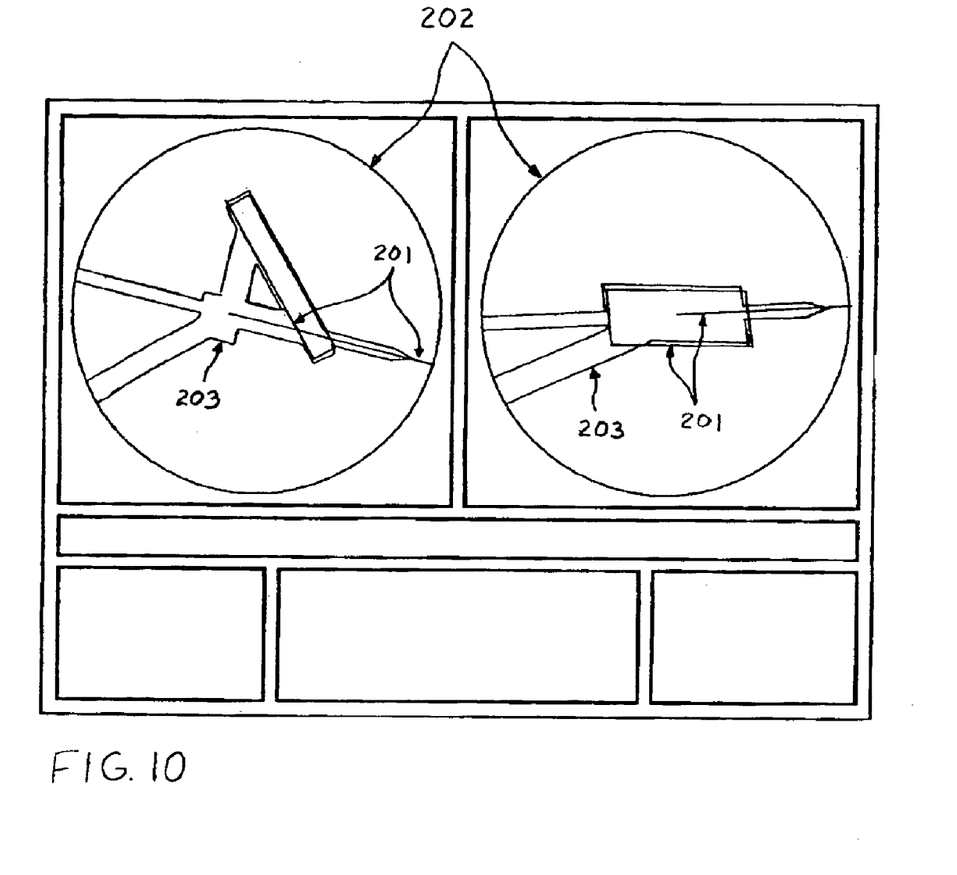
FIG. 10 is an example of a screen display with two images of a surgical instrument with superimposed retained representation.

Existing image guided surgery systems display real-time graphic representations of surgical instruments overlaid on images of the body part. As the instrument moves, so does its graphic representation on the screen and when the instrument is removed from the field its representation disappears from the screen. Likewise, a representation of an implant is only valid as long as the implant is attached to a tracked positioning device. A capability of the computer assisted surgical system described in U.S. Pat. No. 6,285, 902 is the recording of a surgical instrument's pose at the same time an image of the instrument is acquired. As shown in FIG. 10, the instrument's graphic representation (201) is then overlaid on the x-ray images (202) for a period of time that allows the surgeon to verify the accurate functioning of the system by comparing the position of the graphic representation (201) to the instrument's radiographic silhouettes (203) in the x-ray images (202).

An extension of this capability is herein described that improves the surgeon's ability to perform surgery and reduces intraoperative procedure time and radiation exposure. With this invention, the recording of the pose of the instrument occurs at a point in time specified by the surgeon, and an instrument representation is retained immobile on the screen for the purpose of providing the surgeon with information relating to the surgical procedure. The retained instrument representation may be the same as the tracked instrument representation displayed in real time including any real or virtual features, or it may be different from the real-time representation and comprise alternate real or virtual features (e.g., the retained representation for a guide pin may be the cannulated screw that fits over that pin).

Figure 11:
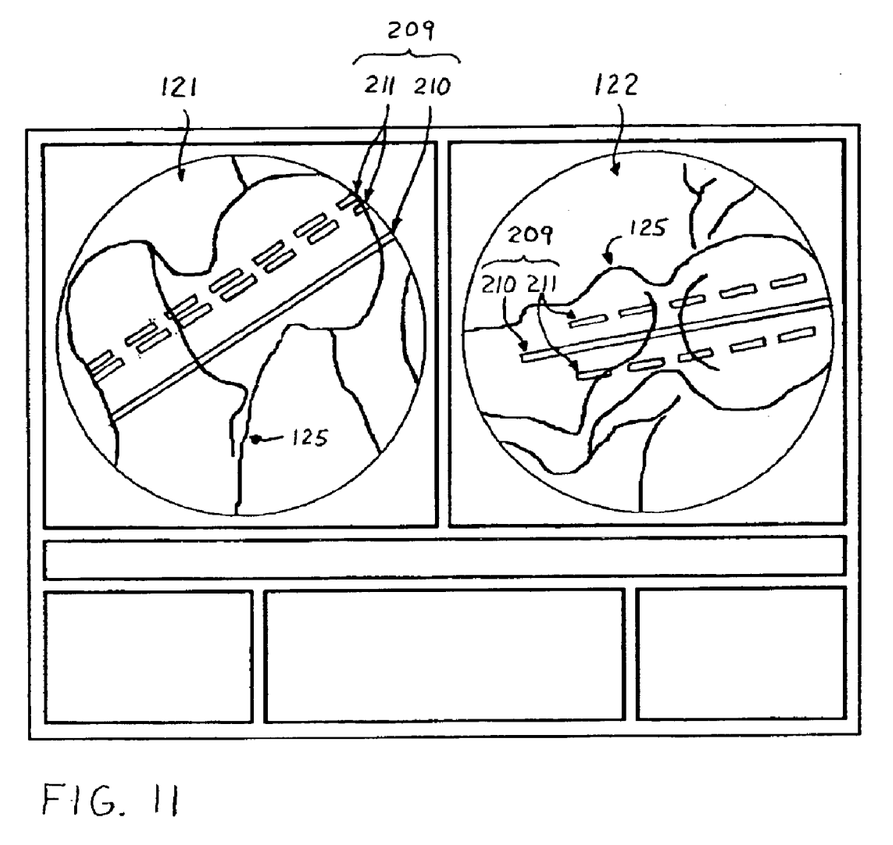
FIG. 11 is an example of a screen display of two images with a superimposed retained representation of the drill guide.
Figure 12:
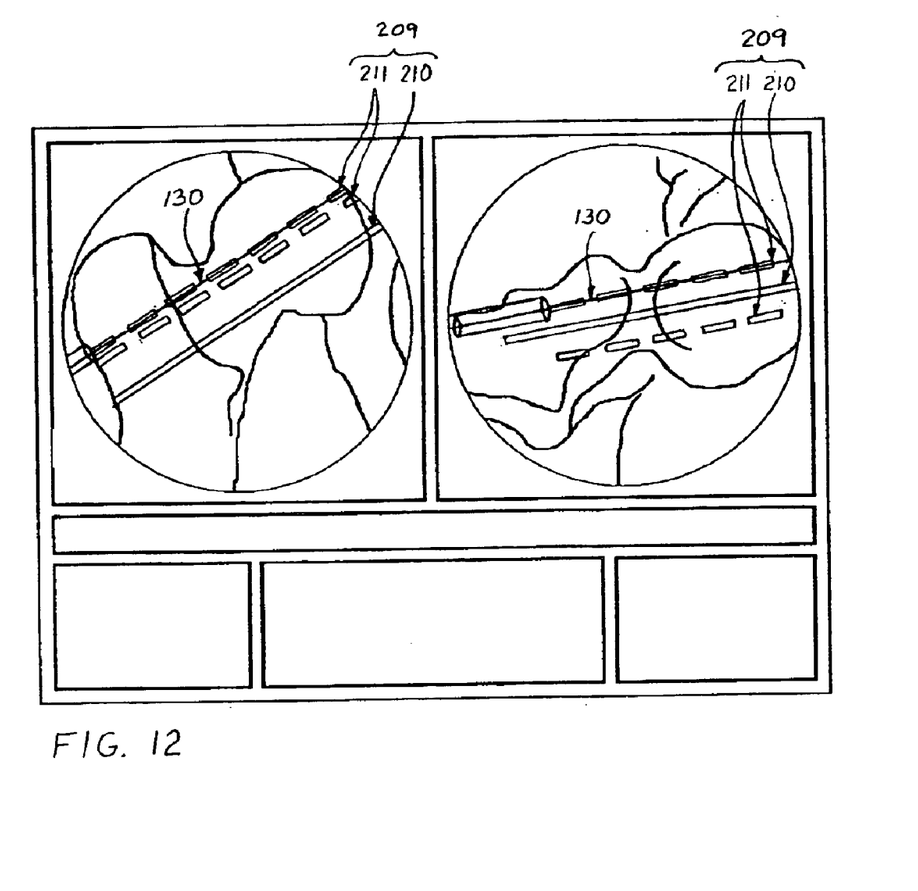
FIG. 12 is an example of a screen display of two images with superimposed representation of the drill guide and a retained representation of the drill guide.

In the preferred embodiment, the invention is an enhancement to the femoral neck fracture fixation procedure previously described. Returning to FIG. 4, the drill guide representation including the real drill guide trajectory (130) and the two virtual trajectories (131) is overlaid on the AP image (121) and lateral image (122) of the femur. Once the drill guide (105) is in the proper position, as evidenced by proper alignment of the drill guide trajectory (130) and the two virtual trajectories (131) in the head and neck of the femur image (125), the surgeon inserts the first guide pin (110). Preferably, with the pin (110) inserted and the drill guide (105) still in position, the surgeon presses a footswitch to cause the pose of the drill guide (105) to be recorded. Thereafter, as shown in FIG. 11, a drill guide representation (209), including the real drill guide trajectory (210) and the virtual trajectories (211), is displayed immobile on the same x-ray images (121 and 122) in the position it occupied relative to the bone (125) when the footswitch was pressed. This retained graphic (209) represents the final position of the first inserted guide pin (210) and the planned trajectories (211) for the subsequent two guide pins. As shown in FIG. 12, the procedure continues with the surgeon using a drill guide representation with a single trajectory representation (130) to insert the final two guide pins relative to the paths indicated by the retained virtual trajectories (211). Additionally, by pressing the footswitch after each remaining guide pin is inserted, a guide pin representation (210) may be retained on the images (121 and 122) in the positions that correspond to the final inserted poses of the guide pins.

The footswitch that the surgeon uses to indicate that the pose of the instrument is to be recorded may be replaced with any other signaling device without departing from the instant invention. Other possibilities include a pushbutton on the instrument, a keypad or keyboard button, a drill trigger, or a voice activated switch In the preferred embodiment, the graphic representations are displayed overlaid on x-ray images. Alternatively, the representations can be displayed overlaid on other medical imaging data (CT, MRI, etc.) or relative to other instruments in a graphic picture not requiring imaging data.

While the described application is for insertion of percutaneous hip screws, other surgical procedures may be addressed without departing from the instant invention. In an alternative embodiment, a probe tip or crosshairs representing the virtual cursor tip described previously can be retained on the screen as a reference marker. Likewise, multiple points, with optional interconnecting lines, may be retained to produce a straight or curved path relative to image or model data. In other alternative embodiments, the graphic representation that is retained on the screen may comprise screws used to hold reduction of a complex fracture or affix an implanted device, an implant or individual components of a multi-component implant, reference marks used in subsequent steps of the procedure, or any other instrument, implant, template, measurement, or graphic information that would benefit the surgeon by being retained in a specified position. Further, the graphic representation to be retained may include real or virtual features, and may be the same or different from the representation that was displayed prior to the recording of the instrument's position.

This invention has utility in numerous other image-guided surgical procedures. Those skilled in the art will recognize the applicability of this invention to other procedures and areas of surgery.

What is claimed is:

1. A method for inserting multiple guide pins into a bone, the method comprising the steps of:
   (a) generating at least one x-ray image of the bone and displaying said at least one x-ray image on a display means;
   (b) positioning a drill guide in the vicinity of the bone, said drill guide comprising a bore portion that defines a real trajectory for drilling;
   (c) generating a graphic representation of the real trajectory and one or more virtual trajectories, said virtual trajectories having fixed and known relationships to the real trajectory and representing possible positions for subsequent real trajectories;
   (d) superimposing the representations of the real trajectory and virtual trajectories over the at least one x-ray image of the bone;
   (e) repositioning the drill guide into a desired position relative to the bone; and
   (f) inserting a guide pin into the bone; wherein the surgeon positions the drill guide based on the alignment of the graphic representations of the real and virtual trajectories relative to the image of the bone.

2. The method of claim 1 wherein steps (a) to (f) are repeated for each guide pin to be inserted and for each guide pin inserted subsequent to the first guide pin the surgeon positions the drill guide based on the alignment of the graphic representations of the one or more virtual trajectories with images of one or more previously placed guide pins.

3. The method of claim 1 wherein the representation of the real trajectory is graphically distinguishable from the representations of the virtual trajectories.

4. The method of claim 1 wherein the insertion of the first guide pin further comprises the steps of:
   (g) recording the pose of the drill guide at the time the guide pin was inserted;
   (h) generating a second graphic representation of the real trajectory and one or more virtual trajectories; and
   (i) retaining a superposition of the graphic representation of the real drilling trajectory and one or more virtual trajectories over the at least one x-ray image of the bone at positions corresponding to the recorded pose; wherein the retained graphic representation of the real and virtual trajectories remains visible for subsequent guide pin insertions.

5. The method of claim 4 wherein steps (a) to (g) are performed for the first guide pin, and steps (a) to (f) are repeated for each subsequent guide pin to be inserted and the graphic representation of the drill guide for the subsequent steps comprises the real trajectory and the surgeon positions the drill guide based on the alignment of the real trajectory with a retained virtual trajectory from step (i).

6. A method for inserting multiple guide pins into a bone, the method comprising the steps of:
   (a) generating at least one image of the bone and displaying said at least one image on a display;
   (b) positioning a drill guide in the vicinity of the bone, the drill guide comprising a bore portion that defines a real trajectory for drilling;
   (c) generating a graphic representation of the real trajectory and one or more virtual trajectories, the virtual trajectories having fixed and known relationships to the real trajectory and representing possible positions for subsequent real trajectories;
   (d) superimposing the representation of the real trajectory and virtual trajectories over the at least one image of the bone;
   (e) repositioning the drill guide into a desired position relative to the bone;
   (f) inserting a guide pin into the bone;
   (g) positioning the drill guide based on the alignment of the graphic representations of the real and virtual trajectories relative to the image of the bone;
   (h) generating a second graphic representation of the real trajectory and one or more virtual trajectories;
   (i) retaining a superposition of the graphic representation of the real drilling trajectory and one or more virtual trajectories over the at least one image of the bone at positions corresponding to a recorded pose; and
   (j) displaying the retained graphic representation of the real and virtual trajectories for subsequent guide pin insertions.

* * * * *